(12) United States Patent
Shakour et al.

(10) Patent No.: US 12,257,058 B2
(45) Date of Patent: Mar. 25, 2025

(54) BRUSH ELECTRODE

(71) Applicant: TECH INNOSPHERE ENGINEERING LTD., Haifa (IL)

(72) Inventors: Ehab Shakour, Haifa (IL); Yousef Badran, Haifa (IL); Rami Shacour, Haifa (IL); Gabriel Shakour, Haifa (IL)

(73) Assignee: TECH INNOSPHERE ENGINEERING LTD., Haifa (IL)

( * ) Notice: Subject to any disclaimer, the term of this patent is extended or adjusted under 35 U.S.C. 154(b) by 0 days.

(21) Appl. No.: 18/120,427

(22) Filed: Mar. 13, 2023

(65) Prior Publication Data

US 2023/0210431 A1 Jul. 6, 2023

Related U.S. Application Data

(63) Continuation of application No. 16/469,207, filed as application No. PCT/IL2017/050934 on Aug. 22, 2017, now Pat. No. 11,647,937.

(Continued)

(51) Int. Cl.
*A61B 5/291* (2021.01)
*A61B 5/266* (2021.01)
(Continued)

(52) U.S. Cl.
CPC ............. *A61B 5/324* (2021.01); *A61B 5/266* (2021.01); *A61B 5/291* (2021.01); *A61N 1/0472* (2013.01);
(Continued)

(58) Field of Classification Search
CPC ......... A61B 5/291; A61B 5/25; A61B 5/6813; A61B 5/6814; A61B 5/6815;
(Continued)

(56) References Cited

U.S. PATENT DOCUMENTS 1,664,457 A 4/1928 Lloyd
4,195,626 A * 4/1980 Schweizer ............. A61B 5/377
600/587

(Continued)

FOREIGN PATENT DOCUMENTS

| CN | 105748065 | 7/2016 |
| EP | 1767147 | 3/2007 |
| GB | 2274396 | 7/1994 |

OTHER PUBLICATIONS

Zhang, Hui, et al., "Textile-Structured Human Body Surface Biopotential Signal Acquisition Electrode." *2011 4th International Congress on Image and Signal Processing.* vol. 5. IEEE, 2011, p. 2792-97.

*Primary Examiner* — Eun Hwa Kim
(74) *Attorney, Agent, or Firm* — PEARL COHEN ZEDEK LATZER BARATZ LLP

(57) ABSTRACT

A brush electrode includes an electrode base that is connectable to an external device that is configured to generate an electrical signal or receive an electrical signal. A plurality of strand electrodes extend outward from the electrode base. A distal end of each strand electrode is configured to contact a skin surface. The strand electrodes are configured to hold an electrolyte to facilitate ionic conduction of the electrical signal to or from the skin surface.

11 Claims, 8 Drawing Sheets

Related U.S. Application Data

(60) Provisional application No. 62/434,954, filed on Dec. 15, 2016.

(51) Int. Cl.
*A61B 5/324* (2021.01)
*A61N 1/04* (2006.01)

(52) U.S. Cl.
CPC . *A61B 2562/0217* (2017.08); *A61B 2562/225* (2013.01); *A61B 2562/227* (2013.01)

(58) Field of Classification Search
CPC ... A61B 5/6816; A61B 5/6824; A61B 5/6825; A61B 5/6828; A61B 5/6829; A61B 2562/046; A61B 2562/2017; A61B 1/0472; A61B 1/322
See application file for complete search history.

(56) References Cited

U.S. PATENT DOCUMENTS

| | | | |
|---|---|---|---|
| 7,326,204 B2 * | 2/2008 | Paul | A61B 18/1402 606/41 |
| 2002/0177767 A1 | 11/2002 | Burton et al. | |
| 2005/0159739 A1 | 7/2005 | Paul et al. | |
| 2007/0105984 A1 | 5/2007 | Griffin | |
| 2011/0054288 A1 * | 3/2011 | Besio | A61B 5/291 600/383 |
| 2011/0237923 A1 * | 9/2011 | Picht | A61B 5/6843 600/383 |
| 2012/0161783 A1 * | 6/2012 | Berka | A61B 5/291 324/600 |
| 2012/0190959 A1 * | 7/2012 | Hayakawa | A61B 5/291 600/383 |
| 2015/0065838 A1 * | 3/2015 | Wingeier | A61B 5/296 600/397 |

\* cited by examiner

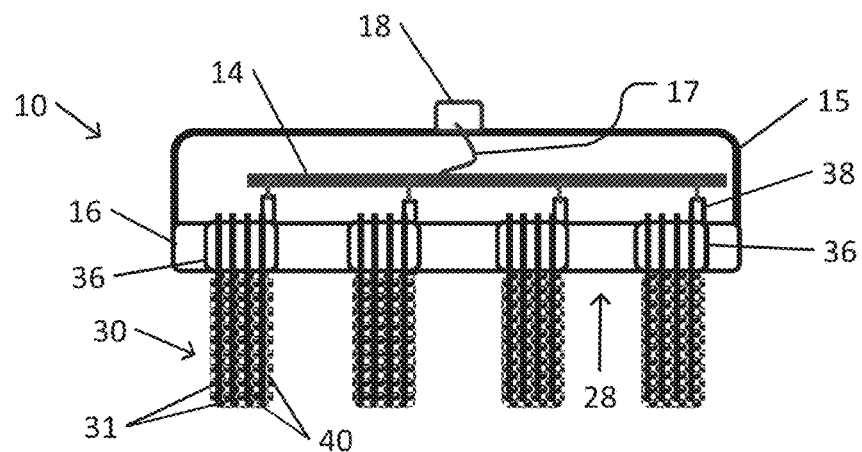
Fig. 4
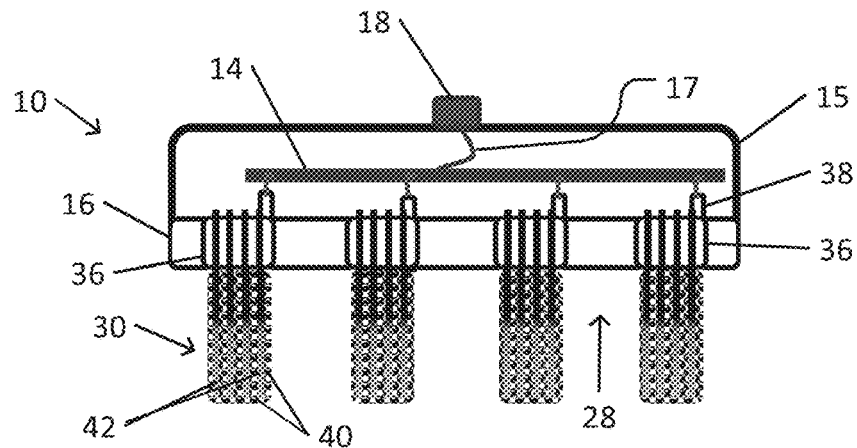 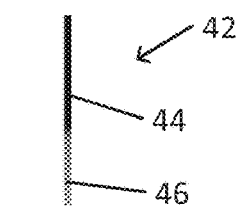
Fig. 5A          Fig. 5B
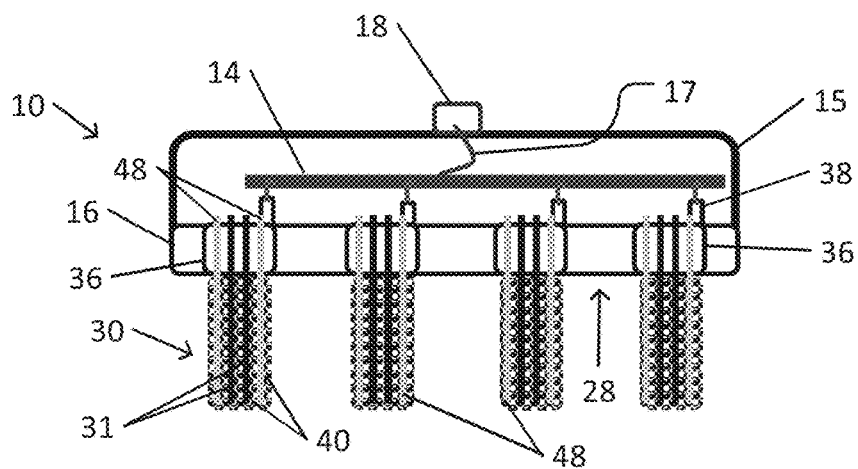
Fig. 6

BRUSH ELECTRODE

CROSS REFERENCE TO RELATED APPLICATIONS

The present application is a Continuation application of U.S. patent application Ser. No. 16/469,207, filed Jun. 16, 2019, which is national phase application of PCT/IL2017/050934, filed Aug. 22, 2017, claiming benefit from U.S. Provisional Patent Application No. 62/434,954, filed Dec. 15, 2016, all of which are incorporated herein by reference in their entirety.

FIELD OF THE INVENTION

The present invention relates to electrodes for contact with a body. More particularly, the present invention relates to a brush electrode.

BACKGROUND OF THE INVENTION

Various medical applications or other applications benefit from electrodes that are noninvasive and sensitive to various electrical signals that are produced by the body of a human, animal, other form of living being. For example, various noninvasive medical diagnostic, therapeutic, or research procedures may utilize such electrodes that are placed on the skin. Such procedures include, for example, electroencephalography (EEG), electrocardiography (ECG), electromyography (EMG) and other diagnostic techniques. A diagnostic or therapeutic technique may include electrical brain stimulation, muscle stimulation, neuronal stimulation, or other types of stimulation.

In some cases, such electrodes may be utilized in a gaming system, in lie detection, in monitoring of a vehicle or machine operator, or in various other situations, in or out of the laboratory.

Typically, an electrode for conducting electrical signals between the skin and an external device is placed or pressed onto the skin at one or more appropriate locations (e.g., near an organ or tissue that produces an electrical signal or that is affected by an externally applied electrical signal). Typically, the interface between the skin and the electrode is not an efficient conductor of electrical signals. Among other reasons, an electronic component operates via conduction of electrical charges in the form of electrons and holes, while electrical signals in physiological organs, tissues, and cells are typically involve movement of electrical charges in the form of positive and negative ions. Conduction of an electrical signal into the body may require a charge conversion by an electrochemical process.

In order to facilitate electrical conduction at the interface between the skin and the electrode, a conductive medium is placed at the interface. For example, the conductive medium may include saline solution (e.g., permeating a sponge or other absorbent material), a conductive gel, or another wet medium. The conductive medium may be placed onto the skin, onto the electrode, or both. For example, some disposable electrodes are pre-embedded in a pad that may include a conductive medium, an adhesive, or both.

SUMMARY OF THE INVENTION

There is thus provided, in accordance with an embodiment of the present invention, a brush electrode including: an electrode base that is connectable to an external device that is configured to generate an electrical signal or receive an electrical signal; and a plurality of strand electrodes that extend outward from the electrode base, a distal end of each strand electrode configured to contact a skin surface, the plurality of strand electrodes configured to hold an electrolyte to facilitate ionic conduction of the electrical signal to or from the skin surface.

Furthermore, in accordance with an embodiment of the present invention, the strand electrodes are clustered into a plurality of clusters of strand electrodes, neighboring clusters of the plurality of clusters being separated from one another by gaps without any strand electrodes.

Furthermore, in accordance with an embodiment of the present invention, a cluster of the plurality of clusters is held to the base by a staple or a ferrule.

Furthermore, in accordance with an embodiment of the present invention, the plurality of clusters are electrically connected to a single external connector for connecting to the external device.

Furthermore, in accordance with an embodiment of the present invention, at least two clusters of the plurality of clusters are connected to different external connectors for connecting separately to the external device.

Furthermore, in accordance with an embodiment of the present invention, the brush electrode includes an isolating barrier for electorally isolating two clusters of the plurality of clusters from one another.

Furthermore, in accordance with an embodiment of the present invention, a distal face of the electrode base includes a plurality of openings, each opening configured to enable the strand electrodes of each cluster of the plurality of clusters to extend distally outward.

Furthermore, in accordance with an embodiment of the present invention, the plurality of openings are arranged in a rectangular array.

Furthermore, in accordance with an embodiment of the present invention, the plurality of strand electrodes are configured to hold the electrolyte by capillary forces.

Furthermore, in accordance with an embodiment of the present invention, a strand electrode of the plurality of strand electrodes includes a hollow core that is configured to be filled with the electrolyte, or is configured to absorb or adsorb the electrolyte.

Furthermore, in accordance with an embodiment of the present invention, a strand electrode of the plurality of strand electrodes is electrically resistive or ionically conducting.

Furthermore, in accordance with an embodiment of the present invention, a proximal segment of a strand electrode of the plurality of strand electrodes is electronically conducting, and a distal segment of that strand electrode is electrically resistive or ionically conducting.

Furthermore, in accordance with an embodiment of the present invention, the brush electrode includes an electrolyte reservoir.

Furthermore, in accordance with an embodiment of the present invention, the plurality of strand electrodes includes strand electrodes of different lengths.

Furthermore, in accordance with an embodiment of the present invention, the electrode base is curved.

Furthermore, in accordance with an embodiment of the present invention, the strand electrodes extend substantially perpendicularly outward from the electrode base.

Furthermore, in accordance with an embodiment of the present invention, the strand electrodes extend outward from the electrode base at an oblique angle to the electrode base.

Furthermore, in accordance with an embodiment of the present invention, the strand electrodes are tilted laterally outward.

Furthermore, in accordance with an embodiment of the present invention, a plurality of neighboring strand electrodes of the plurality of strand electrodes terminate in a single ion-conducting tip.

Furthermore, in accordance with an embodiment of the present invention, a plurality of strand electrodes are fully or partially covered by a sleeve.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIG. 4 schematically illustrates a cross section of a brush electrode as shown in FIG. 3, with an electrolyte solution adhering to the clusters of conductive strand electrodes.

FIG. 5A schematically illustrates a variant of a cross section of a brush electrode as shown in FIG. 4, with segmented strand electrodes that are partially electrically conductive and partially nonconductive.

FIG. 5B schematically illustrates a segmented strand electrode of the brush electrode shown in FIG. 5A.

FIG. 6 schematically illustrates a variant of a cross section of a brush electrode as shown in FIG. 4, where each electrode cluster includes different types of strand electrodes.

DETAILED DESCRIPTION OF THE INVENTION

Figure 1:
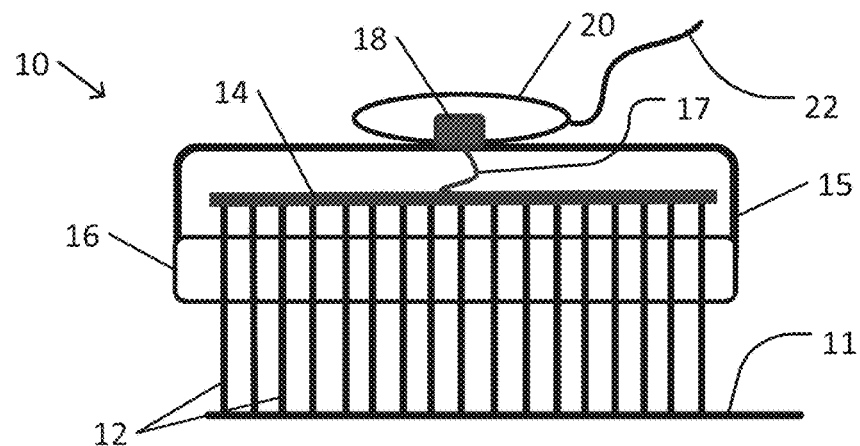
FIG. 1 schematically illustrates a cross section of a brush electrode, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

In accordance with an embodiment of the present invention, an electrode for detecting via skin an electrical signal that is generated by a body (e.g., human, animal, or other living body), or for applying an electrical signal to the body via the skin, is in the form of strand electrodes (having a form suggestive of bristles of a brush). An electrode that includes such strand electrodes is referred to herein as a brush electrode.

A distal end of a strand electrode is configured to be placed against a skin surface of the body and to enable conduction of an electrical signal between the body and an external device. For example, physical properties of the strand electrode (e.g., elasticity, plasticity, or other physical properties) may enable the strand electrode to bend or other accommodate contours of the skin surface while the distal end remains in physical contact with the skin surface. The strand electrode is configured to enable ionic conduction at least at the point of contact. For example, the strand electrode may be made of, covered by (e.g., coated with, e.g., due to hydrophilicity of the strand electrode), or filled with (e.g., absorb or have a hollow core filled with) an ionically conducting material. Alternatively or in addition, the distal end of a strand electrode, or of a group of neighboring strand electrodes, may terminate in an ionically conducting pad or tip. Alternatively or in addition, strand electrodes and the separation distance between the strand electrodes may be configured to hold an ionically conducting substance by capillary forces or otherwise (e.g., hydrophilicity).

A proximal end of each strand electrode may be connected to an electrode base. The electrode base may be connected to an external device. The external device may include a signal generator or other source of an electrical signal that is to be applied to the skin surface or a sensor or detector that is configured to sense or detect as signal that is produced by the body. An electrical signal may thus be conducted by each strand electrode between the external device and the skin surface.

For example, one or more brush electrodes may be configured to facilitate transcranial electric brain stimulation, such as, transcranial direct current stimulation (tDCS), random noise stimulation (RNS), transcranial alternating current stimulation (tACS), or other transcranial stimulation. As another example, one more brush electrodes may be configured to be used in EEG for sensing neural activity of the brain. In some cases, the brush electrodes may be configured to transmit electric stimulation signals at some times and to sense electric signals at other times, or to concurrently transmit and sense, e.g., using different frequencies or frequency ranges.

A brush electrode as described herein may be advantageous over other types of electrodes. For example, other types of electrodes may require spreading a conductive substance, e.g., in the form of a conductive electrolyte solution or gel, over an entire area of the electrode, or over an equivalent area of the skin. Thus, extensive cleanup of the skin, and any hair covering the skin, may be required after use of the electrode. In particular, when the electrode is to be used on a hairy region of skin, such as the head, attaining contact between the electrode and the skin may require shaving that region of the skin. In addition, moving such an electrode about on the skin surface may wet the skin with the conductive substance and effectively increase the area of contact between the electrode and the skin, e.g., reducing precision of a measurement or application of the electric signal.

A brush electrode as described herein in may be used on hair-covered regions without shaving the hair. The distal ends of each electrode strand may reach the skin between hairs. A conductive substance may be held on the strand electrodes, e.g., by capillary forces in the narrow space between adjacent strand electrodes, capillary forces within (e.g., within a hollow core or between braids of) a strand electrode, absorption within a strand electrode, adsorption to the surface of the strand electrode (e.g., by hydrophilicity of the strand electrode), or otherwise. Thus, it may not be necessary to spread the conductive substance over the skin. Thus, wetting of the skin may be reduced in comparison with use of other types of electrodes.

Some or all of the strand electrodes may be conducting, e.g., constructed of a conductive polymer, metal, or other conductive material, or coated with a conducting material. In some cases, the distal end of a strand electrode may be configured to penetrate into the skin, e.g., e.g., a stratum corneum layer, to facilitate electrical conduction between the body and the external device.

A thickness of each strand electrode may be selected for a particular application or type of application. Increasing the thickness of a strand electrode may increase its rigidity. Such increased rigidity may be advantageous where the strand electrode is to be used to penetrate hair, clothing, bandaging, skin, or in other situations where increased rigidity may be advantageous. On the other hand, decreasing the thickness of a strand electrode may increase its flexibility. Increased flexibility may enable the strand electrode to bend in order to increase its area of contact with smooth skin, or may enable accommodating various protrusions, depressions, or openings on the skin surface.

Similarly, a size of a cluster of strand electrodes, a number of strand electrodes in each cluster, or selection of a structure or technique for holding a plurality of adjacent strand electrodes in the form of a cluster, may be configured for a particular application or type of application.

FIG. 1 schematically illustrates a cross section of a brush electrode, in accordance with an embodiment of the present invention.

Brush electrode 10 includes a plurality of strand electrodes 12. Although the cross sectional view of FIG. 1 shows a uniform linear array of strand electrodes 12 for convenience, it should be understood that strand electrodes 12 of a typical brush electrode 10 may be arranged in a two dimensional pattern (e.g., rectangular, circular, polygonal, oval, or other two-dimensional arrangement). A pattern of strand electrodes 12 may include rows, circles, or other arrangements. Strand electrodes 12 may be irregularly or non-uniformly distributed on brush electrode 10.

A distal end of each strand electrode 12 is configured to he placed against a skin surface 11.

Strand electrodes 12 may be configured to adhere to, to absorb, to adsorb, or to otherwise hold a conductive substance, e.g., in the form of an electrolyte solution for conducting ion charges through the electrolyte solution to skin surface 11. In some cases, each strand electrode 12 may be at least partially electrically conductive. Strand electrodes 12 may be configured to facilitate an electrolysis interface with the conductive substance.

Brush electrode 10 includes electrode casing 15. For example, electrode casing 15 may be configured to isolate all parts of strand electrodes 12, e.g., except for exposed distal ends of strand electrodes 12, from contact with any other objects. Electrode casing 15 may be configured to partially or fully isolate strand electrodes 12 e.g., except for exposed distal ends of strand electrodes 12, as well as other internal components of brush electrode 10 from contact with an ambient atmosphere. Thus, electrode casing 15 may function to prevent contact with external objects or with components of the atmosphere (e.g., moisture, suspended particles, or other components of the ambient atmosphere) from interfering with operation of brush electrode 10.

Dimensions of electrode casing 15 may range from having a length of up to 5 mm, a width of up to 5 mm, and a thickness of up to 1 mm, to having a length of up to 100 mm, a width of up to 100 mm, and a thickness of up to 40 mm (or other ratios between length, width and thickness).

Strand electrodes 12 of brush electrode 10 may he held in place, e.g., in a particular arrangement, by electrode base 16. Electrode base 16 may be incorporated into, or attachable to, electrode casing 15. For example, electrode base 16 may include an arrangement of openings through which each strand electrode 12 may extend distally. In some cases, electrode base 16 may be configured to hold clusters of strand electrodes 12 in a particular arrangement of clusters.

Electrode base 16 may be elastic, rigid, or pliable. In some cases, electrode base 16 may be electrically conductive, for example, made of aluminum or another metal, conductive plastic or silicone, or another conductive material. In some cases, electrode base 16 may be made of a nonconductive plastic, silicone, or other nonconductive material. In some cases, electrode base 16 may be made of a combination of one or more materials, including, but not limited to, materials mentioned above. Electrode base 6 may be circular, rectangular, or otherwise shaped, with a surface area in the range of about 1 square centimeter to about 40 square centimeters. For example, a size and shape of electrode base 16, or of brush electrode 10, may be selected to approximately match (e.g., such that strand electrodes 12 cover) a target region of the skin surface to which brush electrode 10 is to be applied.

In the example shown, all strand electrodes 12 extended distally outward in a direction that is substantially perpendicular to electrode base 16. In other examples, some or all of strand electrodes 12 may extend distally outward from electrode base 16 at an oblique angle to electrode base 16.

In some cases, each strand electrode 12 may extend distally outward from electrode base 16 by a distance that is no longer than 3 cm. In some cases, each strand electrode 12 may extend outward from electrode base 16 by less than 2 cm, e.g., between 1 cm and 2 cm.

Strand electrodes 12 may be flexible, elastic, or plastic, e.g., depending on a material from which each strand electrode 12 is constructed, and on a lateral thickness of each strand electrode 12. For example, strand electrode 12 may be constructed of, or may include, conductive or nonconductive PA 6 nylon, PA 6.6 nylon, PA 6,10 nylon, PA 6,12 nylon, or viscose. A strand electrode 12 may be made of Thunderon™, silicone, polyethylene or other polymer, elastomer, metal, agave bristle, animal hair, or other materials. In some cases, strand electrodes 12 may be coated with a conductive material. In some cases, strand electrode 12 is not conductive but is coated with a conductive material.

A lateral thickness (e.g., diameter or other representative distance from one side of a strand electrode 12 to another) may range from 0.01 mm to 1 min, e.g., in a range of lateral thickness from about 0.05 mm to about 0.8 mm, or, more particularly, from about 0.15 mm to about 0.6 mm. A strand electrode 12 may have another lateral thickness.

A density of an arrangement of strand electrodes 12, e.g., on a surface of electrode base 16, may range from about 20 strand electrodes 12 per square centimeter of surface area to about 200 strand electrodes 12 per square centimeter of surface area. In some cases, the density may be selected in accordance with lateral thickness of each strand electrode 12.

Strand electrodes 12 may be made of a material with a volume resistivity ranging from about $10^8$ Ω-cm to less than $10^3$ Ω-cm. Similarly, surface resistivity may range from about $10^8$ Ω/square to less than $10^3$ Ω/square.

According to some embodiments, strand electrode 12 made of different materials, or otherwise having different properties or characteristics, may be included in a single brush electrode 10.

Each strand electrode 12 may be electrically connected to an external device. For example, the external device may be configured to generate an electrical signal, to receive an electrical signal, or both. The external device may be wearable or other portable device, or may be a non-portable, e.g., desktop or other fixed, device. The external device may be battery powered, may be connected to a computer or computing circuitry, or may be otherwise powered.

A proximal end of each strand electrode 12 of brush electrode 10 may be held, e.g., by electrode base 16, in electrical contact with electrode conductor 14. Typically, e.g., when single electrical signal is to be applied concurrently to all strand electrodes 12, or when all strand electrodes 12 are to conduct a single electrical signal from a skin surface 11 to the external device, all strand electrodes 12 may be connected to a single common electrode conductor 14. For example, electrode conductor 14 may be in the form of one or more plates or bars that are constructed of a conducting metal, polymer, or other conducting material. The plates or bars of electrode conductor 14 may be in electrical contact with one another, e.g., directly or via a common conductor to which all of the plates or bars are electrically connected. In some cases, e.g., where different strand electrodes 12 are configured to carry concurrently different electrical signals, electrode conductor 14 may include two or more conducting plates or bars that are not electrically connected to one another.

For example, electrode conductor 14 may be connected via internal conductor 17 (e.g., that includes one or more conducting wires, cables, or bars) to external connector 18. For example, in some cases (e.g., where brush electrode 10 is configured to function in place of a traditional ECG or EEG electrode) external connector 18 may include a simple male snap connector. In other cases, external connector 18 may include another type of connector.

External connector 18 may be connected to an external device by a device connector 20, e.g., that is connected to the external device by device connection 22. For example, where external connector 18 is in the form of a male snap connector, device connector 20 may be in the form of a female snap connector. is other examples, device connector 20 may represent another type of connector. In some cases, device connector 20 may include electrical or electronic circuitry. Device connection 22 may include an electrical cable, or another type of wired or wireless connection to the external device.

In some cases, strand electrodes 12 may be arranged on electrode base 16 in clusters of densely packed strand electrodes 12, with neighboring clusters being separated by gaps with no strand electrodes. The arrangement in clusters may facilitate holding of a conductive substance, e.g., by capillary forces between the surfaces of different strand electrodes 12 in a cluster. The facilitated holding of the conductive substance may increase or facilitate conductivity between strand electrodes 12 and a skin surface 11.

Figure 2:
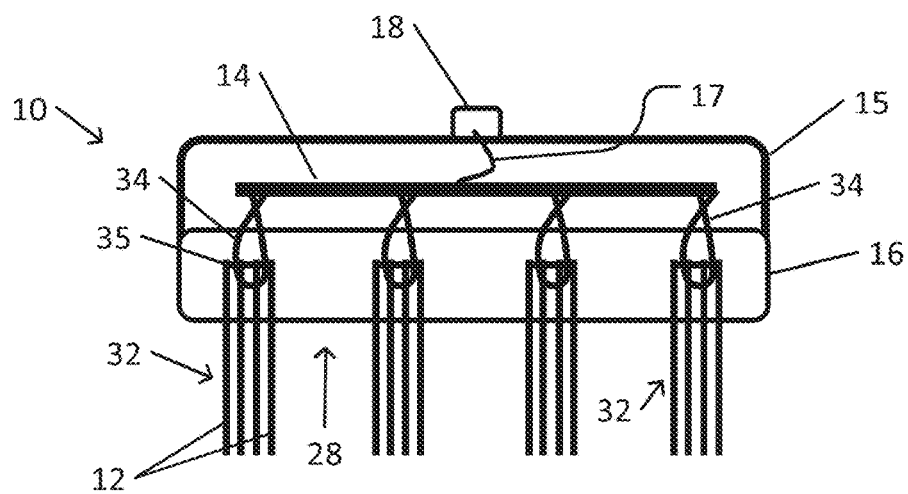
FIG. 2 schematically illustrates a cross section of a brush electrode having strand electrodes arranged in clusters in the form of tufts held in place by staples.

FIG. 2 schematically illustrates a cross section of a brush electrode having strand electrodes arranged in clusters in the form of tufts held in place by staples.

In the example shown, strand electrodes 12 are arranged in clusters in the form of electrode tufts 32. A plurality of strand electrodes 12 in each electrode tuft 32 are connected to one another at their proximal ends. For example, in some cases, the proximal ends of each strand electrode 12 in an electrode tuft 32 may be formed by bending or folding a single strand (e.g., that is approximately twice as long as each strand electrode 12) at proximal bend 35 to form two strand electrodes 12. An electrode tuft 32 may be otherwise formed by a plurality of strand electrodes 12.

Each electrode tuft 32 may be held within electrode base 16 by tuft staple 34. Tuft staple 34 may provide an electrical connection between each strand electrode 12 of electrode tuft 32 and electrode conductor 14. For example, tuft staple 34 may include a wire loop that surrounds both proximal bend 35 and connects to electrode conductor 14 or another part of electrode base 16 or of electrode casing 15. As another example, a tuft staple may be U-shaped, Such a U-shaped staple may be configured such as the base of the U-shape holds proximal bend 35 of each electrode tuft 32 to (e.g., in electrical contact with) electrode base 16 when the arms of the U-shape are inserted into electrode base 16.

Each pair of neighboring electrode tufts 32 is separated by a cluster gap 28.

Figure 3:
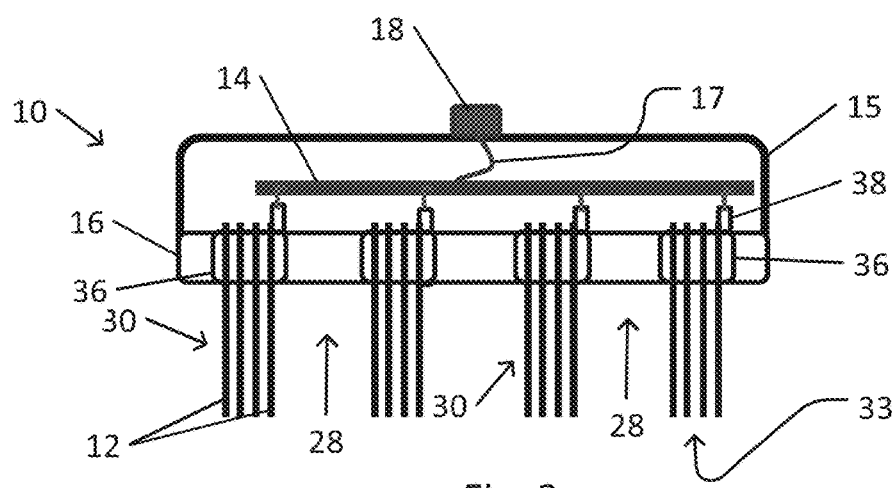
FIG. 3 schematically illustrates a cross section of a brush electrode having clusters of strand electrodes that are held in place by ferrules.

FIG. 3 schematically illustrates a cross section of a brush electrode having clusters of strand electrodes that are held in place by ferrules.

Each electrode ferrule 36 is configured to hold in place within electrode base 16 the proximal ends of a plurality of strand electrodes 12 of an electrode cluster 30. For example, at least an interior part of electrode ferrule 36 may be electrically conducting. Each electrode ferrule 36 may be connected via ferrule connector 38 to electrode conductor 14, or otherwise to an external device. Thus, electrode ferrule 36 may connect strand electrodes 12 in each electrode cluster 30 (e.g., via internal conductor 17 and external connector 18) to the external device. Each pair of neighboring electrode clusters 30 is separated by a cluster gap 28.

For example, the number of strand electrodes 12 in each electrode cluster 30 may range from 5 strand electrodes 12 to more than 20. The lateral thickness of each electrode cluster 30 may be circular or oval, ranging from about 0.5 mm to about 4 mm, and may have a cross-section area of in the range of about 1 square millimeter to about 40 square millimeters. The length of an electrode cluster 30 may range from about 5 mm to about 20 mm.

A density of a distribution of electrode clusters 30, e.g., on a distal surface of electrode base 16, may range from less than 2 electrode clusters 30 per square centimeter to 100 electrode clusters 30 per square centimeter. A representative length of cluster gap 28 (e.g., a minimum distance between adjacent electrode clusters 30) may range from about 0.5 mm to about 8 mm.

When all strand electrodes 12 in an electrode cluster 30 are of equal length and extend perpendicularly distally outward from electrode base 16, then a distal face of electrode cluster 30 may be substantially flat. In some cases, different strand electrodes 12 of a single electrode cluster 30 may have different lengths. In such a case, a distal face 33 of electrode cluster 30 may be substantially flat, perpendicular to strand electrodes 12, and parallel to electrode base 16. In other cases, strand electrodes 12 of different lengths may be arranged to form a distal face that is planar but tilted, convex, or otherwise shaped. A single electrode cluster 30 may include strand electrodes 12 of different materials and dimensions.

A brush electrode 10 may be configured to hold a conductive substance. For example, the conductive substance may be applied by a user of brush electrode 10, e.g., by dipping strand electrodes 12, or an electrode cluster 30, into a conductive substance in the form of a liquid or gel (e.g., an electrolyte solution or other conductive substance in the form of liquid or gel). As another example, a brush electrode 10 may be provided by a producer or vendor of brush electrode 10 with a conductive substance already applied to strand electrodes 12 or to electrode clusters 30 (e.g., within a sealed container, envelope, or packaging.

FIG. 4 schematically illustrates a cross section of brush electrode as shown in FIG. 3, with an electrolyte solution adhering to the clusters of conductive strand electrodes.

As used herein, a strand electrode, or a part of a strand electrode, is considered to be conductive when constructed of an electronically conductive material that is configured to conduct electrical current in the form of electrons (e.g., such as a metal or other electronically conductive substance).

Each electrode cluster 30 is shown as holding conductive substance 40 among electronically conductive strand electrodes 31. For example, conductive substance 40 may be held within electrode cluster 30 by capillary forces among electronically conductive strand electrodes 31.

In the example shown, electronically conductive strand electrodes 31 may be assumed to be conductive so as to facilitate electrolysis, e.g., within conductive substance 40.

Other types of electrodes, or combinations of different types of electrodes, may be included in a brush electrode 10 whose strand electrodes are configured to hold a conductive substance 40.

In an example of a brush electrode 10, an electrode cluster 30 includes approximately 40 strand electrodes (e.g., electrically conductive or otherwise), each about 1.2 mm long with a diameter of about 0.3 mm. In some examples, the strand electrodes may be made of or may include conductive nylon PA6.

The structure of electrode cluster 30 is such that a liquid electrolyte may he held between the strand electrodes by physical or chemical properties of the electrolyte, properties of the surfaces of the strand electrodes, structural properties of electrode cluster 30 (e.g., density or another property of the distribution of the strand electrodes), or a combination of these properties. For example, the strand electrodes may be elastic. Therefore, placing brush electrode 10 on a target region of skin surface 11 may cause the strand electrodes to bend to accommodate any curvature or other topography of skin surface 11 while continuing to hold the electrolyte. The elasticity may enable the strand electrodes to move together without separating from one another, so that at least some of the electrolyte remains held between neighboring strand electrodes to facilitate electrolysis and ionic conduction of an ionic electric signal.

In another example, the elasticity of the strand electrodes may be sufficiently weak (e.g., weaker than physical forces, e.g., capillary forces or surface tension, holding a liquid electrolyte between neighboring strand electrodes) such that a change in the position of one or more strand electrodes, for example by bending, may affect one or more neighboring or adjacent strand electrodes to change position in a similar manner (e.g., by a force transmitted via an electrolyte or other liquid held among the strand electrodes).

FIG. 5A schematically illustrates a variant of a cross section of a brush electrode as shown in FIG. 4, with segmented strand electrodes that are partially electrically conductive and partially nonconductive. FIG. 5B schematically illustrates a segmented strand electrode of the brush electrode shown in FIG. 5A.

As used herein, a strand electrode, or part of a strand electrode, is referred to as nonconductive when that strand electrode, or that part of a strand electrode, does not conduct electrons. The nonconductive strand electrode or part may be electrically insulating (e.g., as defined by a low electric conductivity), or may be configured to primarily conduct electricity by motion of ions. For example, a strand electrode may be ionically conducting if constructed of an ionically conductive material, e.g., of an ion-conducting polymer such as poly(3,4-ethylenedioxythiophene) polystyrene sulfonate (PEDOT:PSS) or another ion-conducting polymer, or may be coated with a conductive substance 40 that is conductive of ions.

In the example shown, proximal segment 44 of each segmented strand electrode 42 is electrically conductive. The electrically conductive proximal segment 44 may facilitate electrolysis within conductive substance 40. Distal region 46 of each segmented strand electrode 42 is electrically nonconductive. Electrically nonconductive distal region 46 may provide a medium to enable conductive substance 40 and ionic charges to reach a skin surface 11 against which distal regions 46 are placed in contact.

FIG. 6 schematically illustrates a variant of a cross section of a brush electrode as shown in FIG. 4, where each electrode cluster includes different types of strand electrodes.

In the example shown, each electrode cluster 30 includes both conductive electronically conductive strand electrodes 31, and nonconductive strand electrodes 48. For example, conductive electronically conductive strand electrodes 31 may facilitate electrolysis, e.g., in conductive substance 40. Nonconductive strand electrodes 48 may function as a medium to enable conductive substance 40 to reach skin surface 11. Nonconductive strand electrodes 48 may be electrically insulating or may be ion conducting.

In other examples, different types of strand electrodes may have different mechanical characteristics, electrical characteristics, chemical characteristics, or may differ with regard to other types of characteristics.

Figure 7:
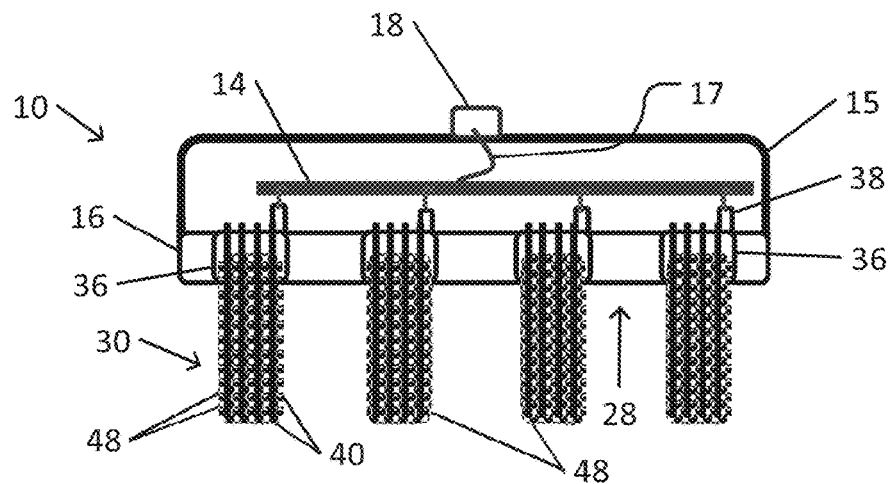
FIG. 7 schematically illustrates a variant of a cross section of a brush electrode as shown in FIG. 4, where electrolysis is configured to occur at a proximal end of each strand electrode.

FIG. 7 schematically illustrates a variant of a cross section of a brush electrode as shown in FIG. 4, where electrolysis is configured to occur at a proximal end of each strand electrode.

In the example shown, conductive substance 40 is present within electrode base 16. For example, conductive substance 40 may be present within each electrode ferrule 36, as shown, or elsewhere within electrode base 16.

In this case may be configured to conduct the ions from electrode base 16 to a skin surface 11 with which the distal ends of the strand electrodes are in contact. In the example shown, strand electrodes in the form of nonconductive strand electrodes 48 are coated with conductive substance 40. Alternatively or in addition, nonconductive strand electrodes 48 may he ionically conductive (e.g., without conductive substance 40), or the strand electrodes may include electronically conductive strand electrodes 31 that are coated with conductive substance 40.

Figure 8:
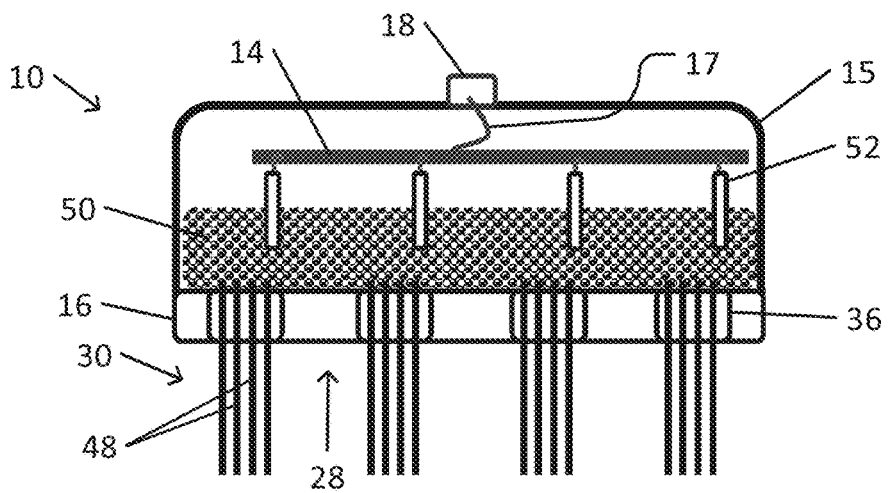
FIG. 8 schematically illustrates an example of a cross section of a brush electrode that includes an electrolyte reservoir within the electrode casing.

FIG. 8 schematically illustrates an example of a cross section of a brush electrode that includes an electrolyte reservoir within the electrode casing.

In the example shown, electrode conductor 14 in connected to a plurality of electrolysis electrodes 52. Each electrolysis electrode is configured to be at least partially immersed in an electrolyte within electrolyte reservoir 50.

In the example shown, electrolyte reservoir 50 is enclosed in electrode casing 15 outside of electrode base 16. Alternatively or in addition, electrolyte reservoir 50 may be located within electrode base 16. Electrolysis may occur within electrolyte reservoir 50, e.g., at electrolysis electrodes 52. The strand electrodes may include nonconductive strand electrodes 48, e.g., that are ionically conducting. Alternatively or in addition, the strand electrodes may include electronically conductive strand electrodes 31 or resistive nonconductive strand electrodes 48 that covered by a conductive substance 40.

In some cases, strand electrodes or electrode clusters of a brush electrode 10 may he configured to facilitate contact of the distal ends of the strand electrodes with a skin surface 11.

Figure 9:
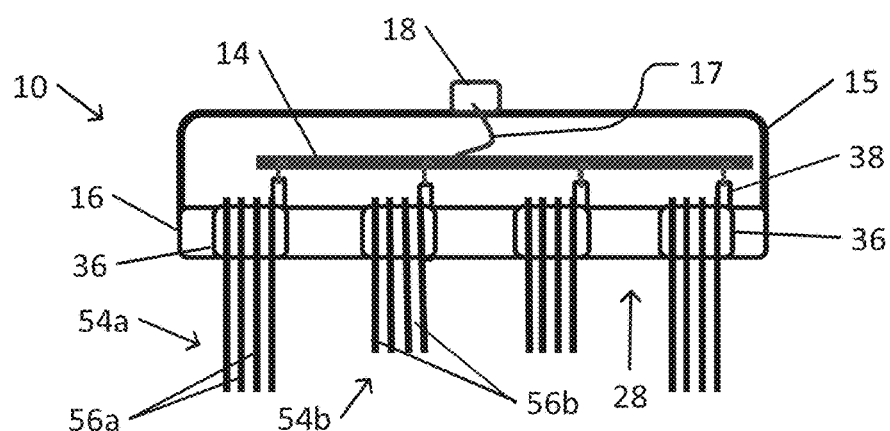
FIG. 9 schematically illustrates a variant of the cross section of a brush electrode shown in FIG. 3, with strand electrodes having different lengths.

FIG. 9 schematically illustrates a variant of the cross section of a brush electrode shown in FIG. 3, with strand electrodes having different lengths.

In the example shown outer electrode clusters 54a are located near a lateral edge of brush electrode 10, while inner electrode clusters 54b are located interior to (e.g., further away from an edge than) outer electrode clusters 54a. In the example shown, strand electrodes 56a of outer electrode clusters 54a are longer than strand electrodes 56b of inner electrode clusters 54b. This configuration may facilitate contact of the distal ends of strand electrodes 56a and 56b with a convex skin surface 11 (e.g., a head, limb, or other convex surface).

In other examples, inner strand electrodes 56b may be longer than outer strand electrodes 56a, e.g., to facilitate contact with a concave skin surface 11.

Typically, a brush electrode 10 may include more than four electrode clusters (e.g., more than in the example shown). In such a case, the lengths of the strand electrodes in the electrode clusters may gradually increase or decrease with increasing distance from a center of that brush electrode 10.

Figure 10:
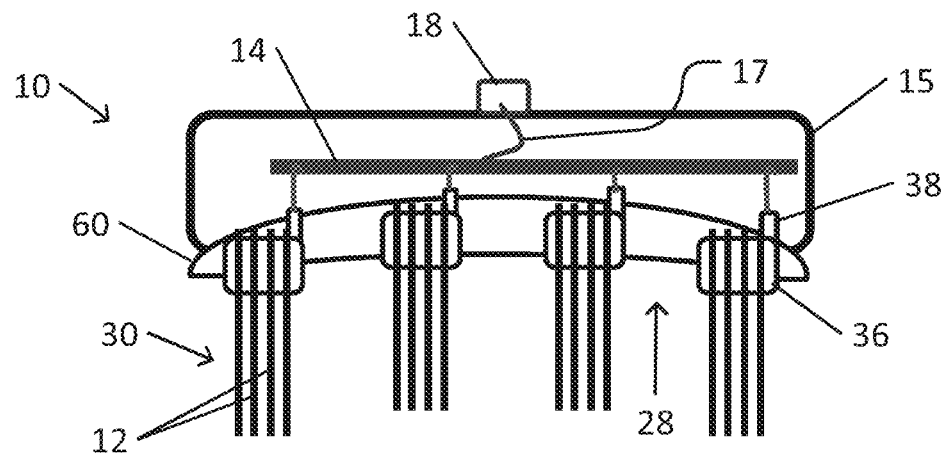
FIG. 10 schematically illustrates a variant of the cross section of a brush electrode shown in FIG. 3, having a curved electrode base.

FIG. 10 schematically illustrates a variant of the cross section of a brush electrode shown in FIG. 3, having a curved electrode base.

In the example shown, all strand electrodes 12 have the same length. However, curved electrode base 60 is concave (e.g., as viewed from the direction of a skin surface 11). Such a concave curved electrode base 60 may facilitate contact of the distal ends of strand electrodes 12 (e.g., where all strand electrodes 12 extend distally by equal lengths from a connection of each strand electrode 12 with concave curved electrode base 60) with a convex skin surface 11 (e.g., on a head, limb, or other convex surface).

In other examples, curved electrode base 60 may be convex, e.g., to facilitate contact of the distal ends of strand electrodes 12 with a concave skin surface 11 (e.g., at an inner joint in a limb or in the neck region).

In some cases, a brush electrode 10 ay include both electrode clusters of different lengths and a curved electrode base 60.

Figure 11:
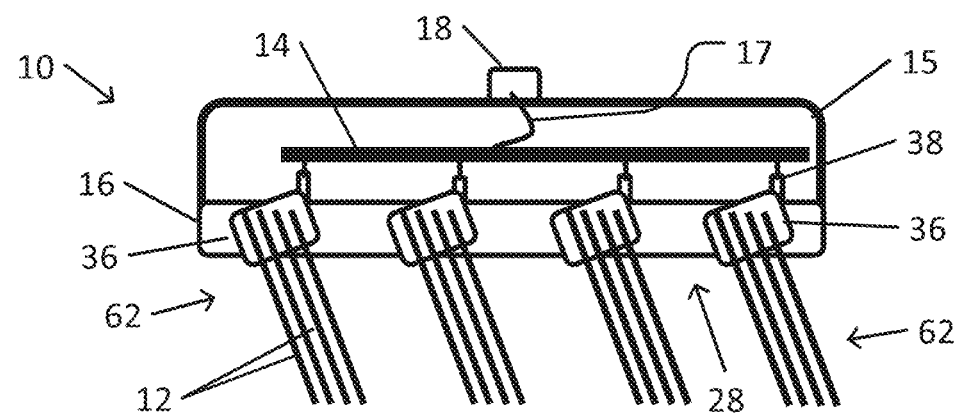
FIG. 11 schematically illustrates a variant of the cross section of a brush electrode shown in FIG. 3, having tilted strand electrodes.

FIG. 11 schematically illustrates a variant of the cross section of a brush electrode shown in FIG. 3, having tilted strand electrodes.

Strand electrodes 12 of each tilted electrode cluster 62 extend distally outward at an oblique angle to (e.g., the distal face of) electrode base 16. For example, the tilt of each tilted electrode cluster 62 may facilitate penetration of hair to an underlying skin surface 11, or may increase comfort of a subject whose skin is contacted by strand electrodes 12.

Figure 12:
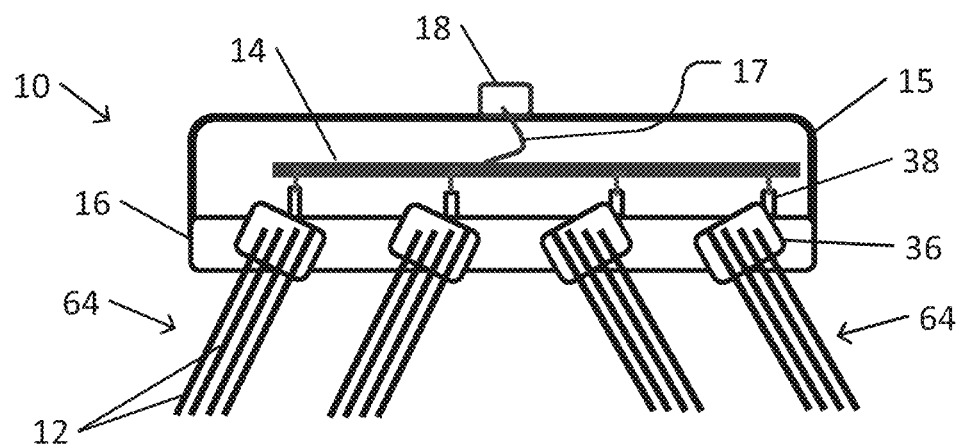
FIG. 12 schematically illustrates a variant of the cross section of a brush electrode shown in FIG. 11, having strand electrodes that are tilted laterally outward.

FIG. 12 schematically illustrates a variant of the cross section of a brush electrode shown in FIG. 11, having strand electrodes that are tilted laterally outward.

In the example shown, strand electrodes 12 of each outwardly tilted electrode cluster 64 are tilted laterally outward (e.g., such that their distal end of each strand electrode 12 is further from a center of brush electrode 10 than its proximal end), each at an oblique angle to (e.g., the distal face of) electrode base 16. The laterally outward tilt may, in addition to facilitating hair penetration and promoting comfort, may contribute to stability of placement of brush electrode 10 on a skin surface 11. For example, the outward lateral tilt may impede lateral sliding of brush electrode 10 across skin surface 11.

In other examples, outwardly tilted electrode cluster 64 may have other orientations. For example, in addition to a laterally outward tilt, each outwardly tilted electrode cluster 64 may also have an azimuthal tilt or slant. The azimuthal slant may, in some cases, enable placement of brush electrode 10a skin surface 11 with a lateral twisting motion. Such an azimuthal slant may further facilitate hair penetration and contact of strand electrodes 12 with a skin surface 11.

In some cases, different parts of a brush electrode 10 may be configured to apply or sense different electrical signals, or to facilitate placement of different brush electrodes 10 in close proximity to one another, e.g., to facilitate application or sensing of different electrical signals.

Figure 13:
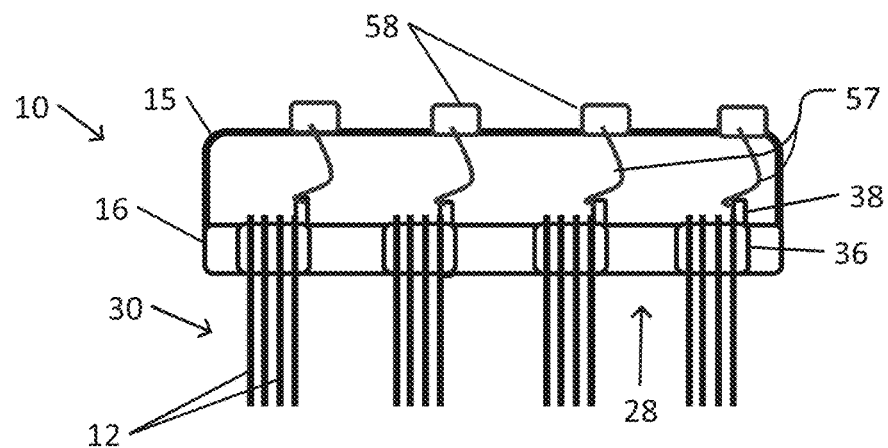
FIG. 13 schematically illustrates a variant of the cross section of a brush electrode shown in FIG. 3, configured to separately connect each electrode cluster to an external device.

FIG. 13 schematically illustrates a variant of the cross section of a brush electrode shown in FIG. 3, configured to separately connect each electrode cluster to an external device.

In the example shown, each electrode cluster 30 is connected to a separate external connector 58 via a separate internal conductor 57. Each external connector 58 may be separately connected to a different external device, or to a different port or connector of the external device. Thus, a different electrical signal may be separately applied to each electrode cluster 30, or may be separately sensed via each electrode cluster 30. For example, in some cases, an electrical signal may be applied to one or more electrode clusters 30, while an electrical signal may be concurrently sensed by one or more other electrode clusters 30.

In other examples, groups of two or more electrode clusters 30 (e.g., neighboring electrode clusters 30) may be connected to different external connectors 58.

Figure 14:
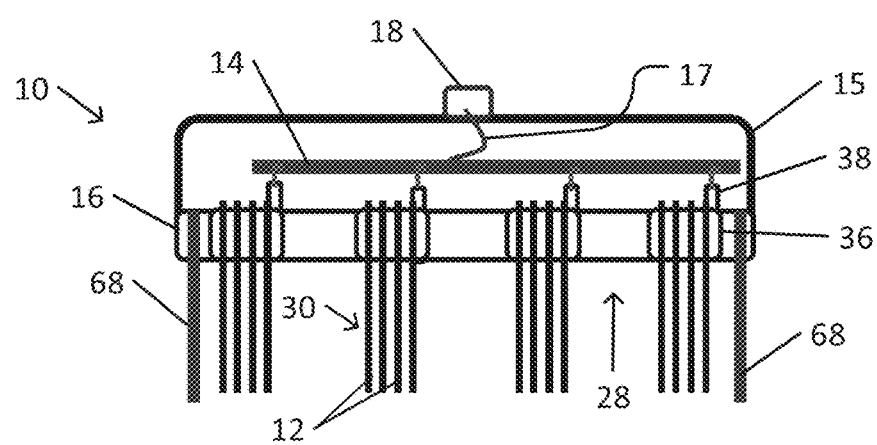
FIG. 14 schematically illustrates a variant of the cross section of a brush electrode shown in FIG. 3, with isolating barriers.

FIG. 14 schematically illustrates a variant of the cross section of a brush electrode shown in FIG. 3, with isolating barriers.

Isolating barriers 68 may be electrically insulating. Isolating barriers 68 may enable placement of two brush electrodes 10 in close proximity to one another. In this case, isolating barriers 68 may prevent contact between strand electrodes 12 or conductive substances 40 of adjacent brush electrodes 10. Isolating barriers 10 may include a hydrophobic material to inhibit passage or water or of water-based substances, or may be water absorptive to absorbing any electrolyte that may otherwise seep between isolating barriers 68 and skin surface 11.

Figure 15:
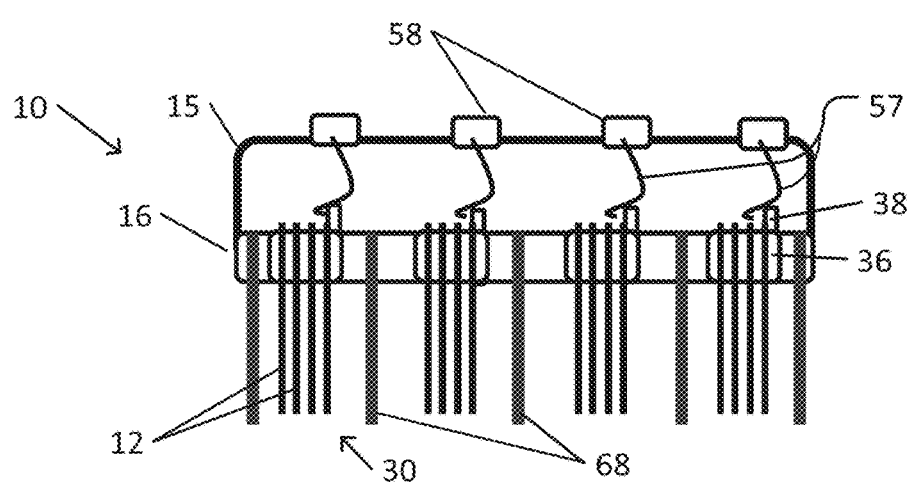
FIG. 15 schematically illustrates a variant of the cross section of a brush electrode shown in FIG. 13, having isolating barriers between electrode clusters.

FIG. 15 schematically illustrates a variant of the cross section of a brush electrode shown in FIG. 13, having isolating barriers between electrode clusters.

Isolating barriers 68 may prevent contact between strand electrodes 12 of neighboring electrode clusters 30. This may be advantageous especially when a different electrical signal is applied to, or is sensed by, each electrode cluster 30.

In some cases, electrical ionic contact between strand electrodes 12 and a skin surface 11 may be facilitated by connecting the distal ends of groups of one or more strand electrodes 12 to an ionically conducting tip.

Figure 16:
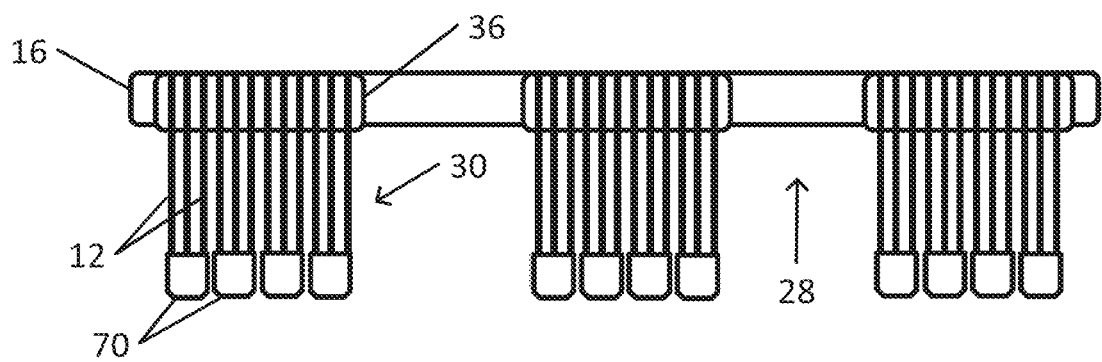
FIG. 16 schematically illustrates a variant of the cross section of a brush electrode shown in FIG. 3, where the distal ends of groups of strand electrodes within a single electrode cluster terminate in an ion-conducting tip.

FIG. 16 schematically illustrates a variant of the cross section of a brush electrode shown in FIG. 3, where the distal ends of groups of strand electrodes within a single electrode cluster terminate in an ion-conducting tip.

In the example shown, each group of neighboring strand electrodes 12 within an electrode cluster 30 terminates in a single ion-conducting tip 70. For example, strand electrodes 12 may be electronically conductive and ion-conducting tip 70 may be made of an ionically conductive material.

Figure 17:
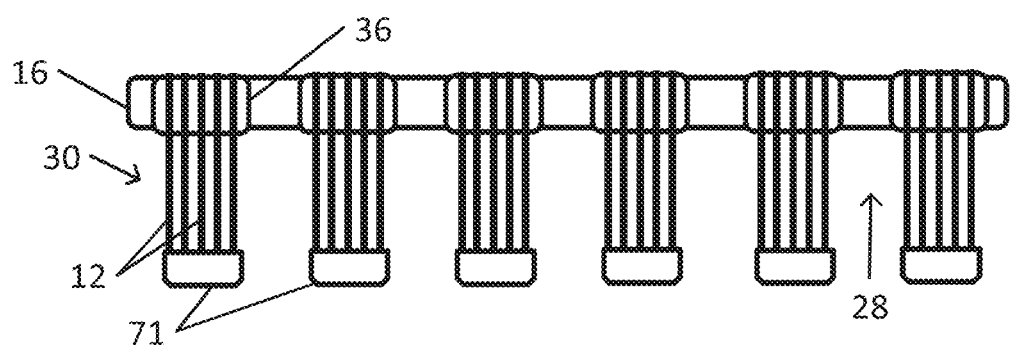
FIG. 17 schematically a variant of the cross section of a brush electrode shown in FIG. 3, where all strand electrodes in an electrode cluster terminate in a single ion-conducting tip.

FIG. 17 schematically a variant of the cross section of a brush electrode shown in FIG. 3, where all strand electrodes in an electrode cluster terminate in a single ion-conducting tip.

Distal ends of all strand electrodes 12 in a single electrode cluster 30 terminate in a single ion-conducting cluster tip 71.

Figure 18:
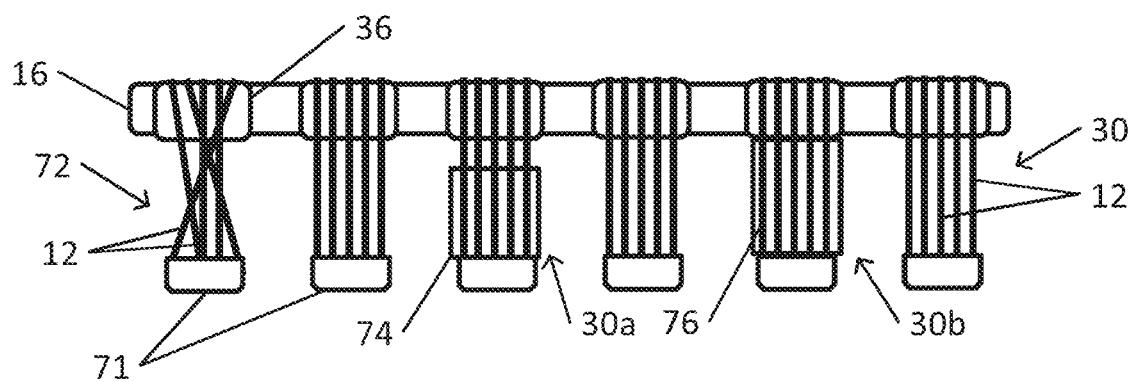
FIG. 18 schematically illustrates variants of electrode clusters of the cross section of a brush electrode shown in FIG. 17.

FIG. 18 schematically illustrates variants of electrode clusters of the cross section of a brush electrode shown in FIG. 17.

For example, interwoven electrode cluster 72 may include strand electrodes 12 that are braided, twisted together, or otherwise interwoven or interlocked.

In electrode cluster 30a, distal segments of strand electrodes 12 are covered by partial sleeve 74. Partial sleeve 74 may enable wetting of the distal segments with an electrolyte without wetting skin surface 11. The electrolyte may be introduced at a proximal end of partial sleeve 74. For example, partial sleeve 74 may be constructed of silicone, nylon, or another material that is flexible and impermeable to an electrolyte.

In electrode cluster 30b, strand electrodes 12 are completely covered by full sleeve 76. Full sleeve 76 may enable wetting of the entire lengths of strand electrodes 12 without wetting skin surface 11. The electrolyte may be introduced into full sleeve 76, e.g., from within electrode base 16 or elsewhere within electrode casing 15. For example, full sleeve 76 may he constructed of silicone, nylon, or another material that is flexible and impermeable to an electrolyte.

Strand electrodes may have various forms, e.g., in addition to those of electronically conductive strand electrode 31, segmented strand electrode 42, and nonconductive strand electrode 48, described above.

Figure 19:
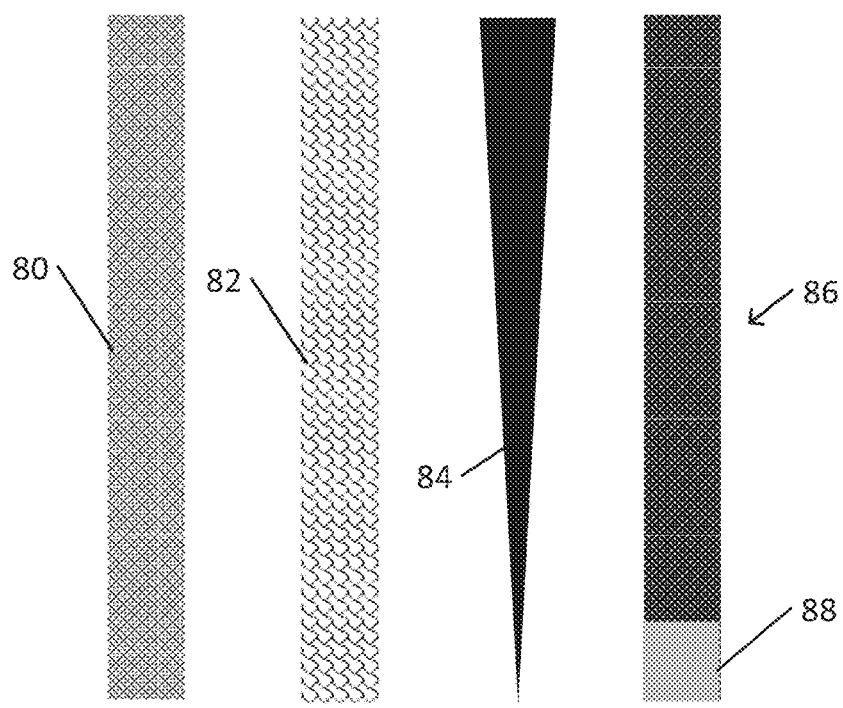
FIG. 19 schematically illustrates variants in the forms of longitudinal cross sections strand electrodes for a brush electrode as shown in FIG. 1.

FIG. 19 schematically illustrates variants in the forms of longitudinal cross sections strand electrodes for a brush electrode as shown in FIG. 1.

Porous strand electrode 80 may be constructed of a porous material, e.g., to facilitate adherence of a conductive substance 40. Braided strand electrode 82 may be constructed of a plurality of braided or interwoven thin strands, e.g., to enable absorption of an electrolyte. A diameter or other lateral dimension of non-uniform profile strand electrode 84 may vary along its length, either monotonically, as in the example shown, or otherwise. Tipped strand electrode 86 may include an ion-conducting electrode tip 88.

Strand electrodes may be constructed with different transverse cross-sectional shapes.

Figure 20:
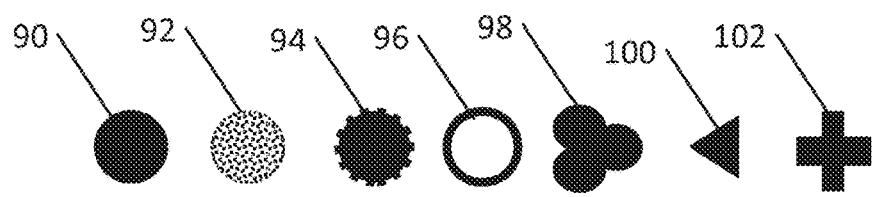
FIG. 20 schematically illustrates variants of a transverse cross-sectional shape of a strand electrode for a brush electrode as shown in FIG. 1.

FIG. 20 schematically illustrates variants of a transverse cross-sectional shape of a strand electrode for a brush electrode as shown in FIG. 1.

Cross sectional shapes may include, for example, solid circular 90, porous circular 92 (e.g., to enable absorption of an electrolyte), serrated 94 (e.g., to facilitate adsorption of an electrolyte), hollow circular 96 (e.g., to enable holding an electrolyte within the strand electrode), trefoil 98, triangular 100 (or other regular polygonal), cross-shaped 102 (or other irregular polygonal), or other shapes (e.g., oval, hollow, porous, or solid variants, or other shapes, such as ovals or other shapes).

Selection of a form of a strand electrode may be determined, at least in part, by various electrical, chemical, or mechanical properties for a particular application.

Although electrode base 16 has been shown in cross section in FIGS. 1-18, electrode base 16 typically extends in two lateral dimensions (e.g., length and width, in addition to its thickness or height).

Figure 21:
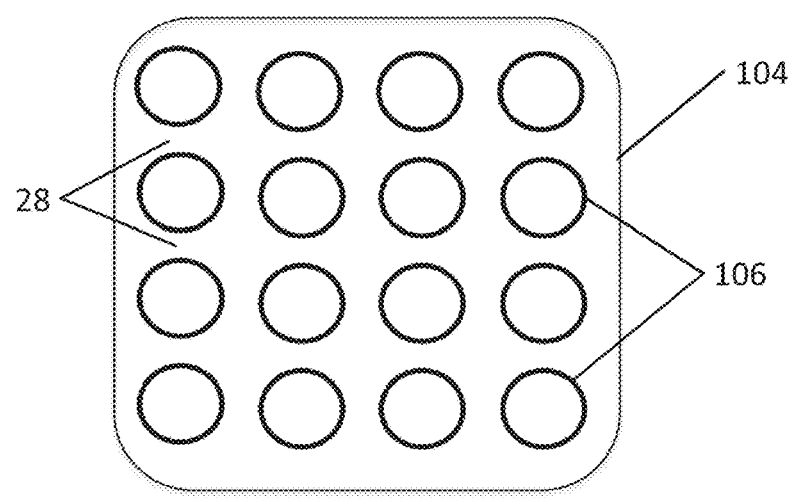
FIG. 21 schematically illustrates a face of an electrode base of a brush electrode as shown in cross section in FIG. 3.

FIG. 21 schematically illustrates a face of an electrode base of a brush electrode as shown in cross section in FIG. 3.

Electrode base face plate 104 is configured to cover a distal face of electrode base 16 (e.g., a face that faces skin surface 11 when in use). Each electrode cluster opening 106 is configured to enable an electrode cluster 30 to extend distally outward through electrode base face plate 104. Spaces between electrode cluster openings 106 may determine the sizes of cluster gaps 28.

Although in the example shown, electrode cluster openings 106 are arranged in a rectangular array, other arrangements are possible. The arrangement and distribution (e.g., diameter or other lateral size, spacing between, or other characteristics of the arrangement or distribution) of electrode cluster openings 106 may be selected as appropriate to a particular application of a brush electrode 10.

Figure 22:
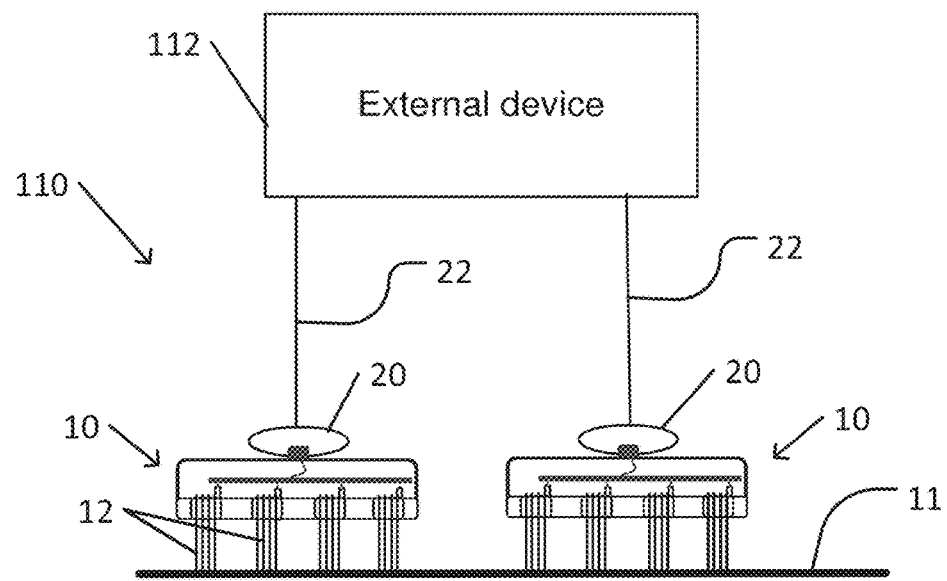
FIG. 22 schematically illustrates a system that includes a plurality of brush electrodes, in accordance with an embodiment of the present invention.

FIG. 22 schematically illustrates a system that includes a plurality of brush electrodes, in accordance with an embodiment of the present invention.

Brush electrode system 110 includes an external device 112 that is connected to a plurality of brush electrodes 10.

External device 112 may include one or more devices. For example, a device of external device 112 may be configured to generate one or more electrical signals that may be applied to skin surface 11 via brush electrodes 10. A device of external device 112 may be configured to sense an electrical signal (e.g., an EEG signal or other signal) that is generated within a body and that may be detected by a brush electrode 10 in contact with skin surface 11.

Each brush electrode 10 may be configured to enable identification by external device 112. For example, an identification mechanism may include application of Inter-Integrated Circuit ($I^2C$) technology, or may include providing each brush electrode 10 with a unique impedance footprint that is identifiable by external device 112. The identification mechanism or a database that is accessible by a processor of external device 112 may enable identification of one or more features or characteristics of each brush electrode 10. Such features and characteristics may include, for example, contact area, configuration of strand electrodes 12, or other features or characteristics.

For example, external device 112 may be connected by one or more device connections 22 to one or more device connectors 20. Each device connector 20 may be connected to a separate brush electrode 10.

Figure 23:
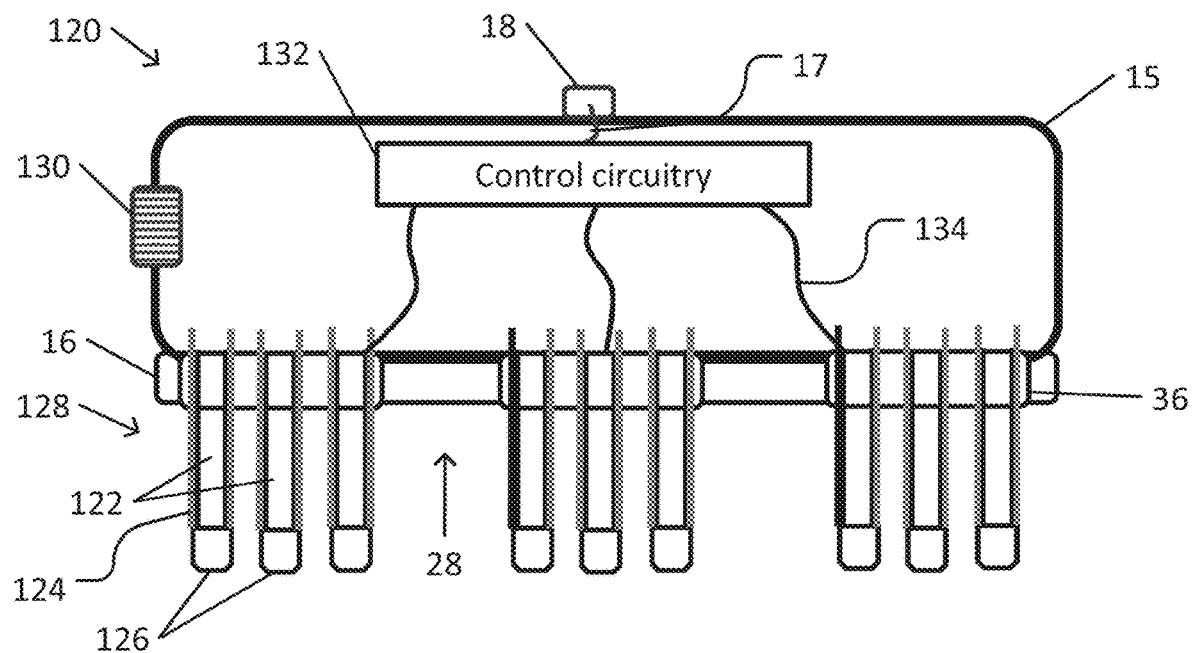
FIG. 23 schematically illustrates a brush electrode with hollow strand electrodes, in accordance with an embodiment of the present invention.

FIG. 23 schematically illustrates a brush electrode with hollow strand electrodes, in accordance with an embodiment of the present invention.

In brush electrode 120, hollow strand electrodes 122 are organized in clusters 128. Control circuitry 132 may be electrically connected to each cluster 128 by cluster conductor 134.

Each hollow strand electrode 122 has a hollow core and is coated with insulating coating 124. Insulating coating 124 may prevent electrical contact between adjacent hollow strand electrodes 122. A distal end of each hollow strand electrode 122 terminates in an ion-conducting tip 126.

An electrolyte may he introduced into electrode casing 15 via electrolyte orifice 130. For example, electrolyte orifice 130 may be configured to enable electrolyte to flow into electrode casing 15, and to impede or prevent outflow of electrolyte from electrode casing 15.

The electrolyte may flow from electrode casing 15 into the hollow core of each hollow strand electrode 122. Thus, electrolysis may occur within each hollow strand electrode 122. The ionic current may be conducted via ion-conducting tip 126 into a skin surface with which ion-conducting tip 126 is in contact.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A brush electrode configured for sending or receiving an electrical signal to or from the skin surface, comprising:
    an electrode base that is connectable to an external device that is configured to generate or receive an electrical signal; and
    a plurality of strand electrodes that extends outward from the electrode base, a distal end of each strand electrode configured to contact a skin surface, said plurality of strand electrodes configured to facilitate conduction of the electrical signal to the skin surface or the physiological signal from the skin surface,
    wherein the plurality of strand electrodes are clustered into a plurality of clusters of strand electrodes, neighboring clusters of the plurality of clusters being separated from one another by gaps without any strand electrodes, wherein the strand electrodes of each of the plurality of clusters of strand electrodes are configured to hold an electrolyte to facilitate ionic conduction,
    wherein each of the strand electrodes of the plurality of clusters extends outward from the electrode base at an oblique angle to the base electrode such that all the strand electrodes of some of the plurality of clusters define a length that is different from a length of all the strand electrodes of some neighboring clusters of said plurality of clusters.

2. The brush electrode of claim 1, wherein a cluster of said plurality of clusters is held to the base by a staple or a ferrule.

3. The brush electrode of claim 1, wherein said plurality of clusters are electrically connected to a single external connector for connecting to the external device.

4. The brush electrode of claim 1, wherein at least two clusters of said plurality of clusters are connected to different external connectors for connecting separately to the external device.

5. The brush electrode of claim 1, further comprising an isolating barrier for electrically isolating two clusters of said plurality of clusters from one another.

6. The brush electrode of claim 1, wherein said plurality of strand electrodes are configured to hold the electrolyte by capillary forces.

7. The brush electrode of claim 1, wherein a strand electrode of said plurality of strand electrodes includes a hollow core that is configured to be filled with the electrolyte or that is configured to absorb or adsorb the electrolyte.

8. The brush electrode of claim 1, wherein a strand electrode of said plurality of strand electrodes is electrically resistive or ionically conducting.

9. The brush electrode of claim 1, wherein a proximal segment of a strand electrode of said plurality of strand electrodes is electronically conducting, and a distal segment of that strand electrode is electrically resistive or ionically conducting.

10. The brush electrode of claim 1, further comprising an electrolyte reservoir.

11. The brush electrode of claim 1, wherein all the plurality of clusters of strand electrodes together define a distal face that is concave with respect to the skin surface.

* * * * *